(12) United States Patent
Okita (10) Patent No.: US 9,877,640 B2
(45) Date of Patent: Jan. 30, 2018

(54) SCANNING ENDOSCOPE HAVING PROPAGATION PORTION WITH LIGHT ABSORBING PORTION OR LIGHT REFLECTING PORTION ON DISTAL END FACE THEREOF

(71) Applicant: OLYMPUS CORPORATION, Tokyo (JP)

(72) Inventor: Yoshinari Okita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/252,807

(22) Filed: Aug. 31, 2016

(65) Prior Publication Data

US 2016/0367125 A1 Dec. 22, 2016

Related U.S. Application Data

(63) Continuation of application No. PCT/JP2015/073867, filed on Aug. 25, 2015.

(30) Foreign Application Priority Data

Nov. 26, 2014 (JP) .................................. 2014-239158

(51) Int. Cl.
*A61B 1/07* (2006.01)
*A61B 1/00* (2006.01)
(Continued)

(52) U.S. Cl.
CPC .................. *A61B 1/07* (2013.01); *A61B 1/00* (2013.01); *A61B 1/00096* (2013.01);
(Continued)

(58) Field of Classification Search
CPC ......... A61B 1/07; A61B 1/00; A61B 1/00096; A61B 1/0676; A61B 1/00172;
(Continued)

(56) References Cited

U.S. PATENT DOCUMENTS 4,019,051 A * 4/1977 Miller .................. G02B 6/2852
250/227.16
4,201,443 A * 5/1980 Hodge ................. G02B 6/3841
250/227.24
(Continued)

FOREIGN PATENT DOCUMENTS

JP 08-227040 A 9/1996
JP 2008-165236 A 7/2008
(Continued)

OTHER PUBLICATIONS

International Search Report dated Nov. 24, 2015 issued in corresponding International Patent Application No. PCT/JP2015/073867.

*Primary Examiner* — John P Leubecker
(74) *Attorney, Agent, or Firm* — Scully, Scott, Murphy & Presser, P.C.

(57) ABSTRACT

A scanning endoscope includes: an optical fiber that emits an illuminating light from a distal end; an actuator that causes a distal end of the optical fiber to oscillate; a fixing block that fixes the optical fiber; and a propagation portion that is provided in close contact with an outer circumferential face of a cladding of the optical fiber at a position on the distal end side relative to the fixing block, and on which, among the illuminating light, light that reaches the outer circumferential face of the cladding is incident and is propagated or absorbed inside the propagation portion.

9 Claims, 4 Drawing Sheets

(51) Int. Cl.
  *G02B 23/26* (2006.01)
  *A61B 1/06* (2006.01)
  *G02B 23/24* (2006.01)
  *G02B 26/10* (2006.01)
  *G02B 21/00* (2006.01)

(52) U.S. Cl.
  CPC ........ *A61B 1/00195* (2013.01); *A61B 1/0676* (2013.01); *G02B 21/0028* (2013.01); *G02B 23/2469* (2013.01); *G02B 23/26* (2013.01); *G02B 26/103* (2013.01)

(58) Field of Classification Search
  CPC .............. A61B 5/0062; G02B 21/0028; G02B 23/2469; G02B 23/26; G02B 26/103
  See application file for complete search history.

(56) References Cited

U.S. PATENT DOCUMENTS

| | | | | |
|---|---|---|---|---|
| 4,352,565 A | * | 10/1982 | Rowe | G01B 9/02094 356/502 |
| 4,633,170 A | * | 12/1986 | Burns | G01R 23/17 324/76.37 |
| 4,962,996 A | * | 10/1990 | Cuellar | C03C 25/106 385/128 |
| 5,926,592 A | * | 7/1999 | Harris | G02B 21/0024 385/127 |
| 7,129,472 B1 | * | 10/2006 | Okawa | A61B 1/00059 250/216 |
| 2002/0048293 A1 | * | 4/2002 | Malone | G02B 6/4206 372/29.011 |
| 2007/0217738 A1 | * | 9/2007 | Anderegg | G02B 6/26 385/29 |
| 2007/0280614 A1 | * | 12/2007 | Karasawa | A61B 1/00096 385/123 |
| 2008/0161648 A1 | * | 7/2008 | Karasawa | A61B 1/00096 600/182 |
| 2009/0024191 A1 | * | 1/2009 | Seibel | A61B 1/0008 607/92 |
| 2009/0103882 A1 | * | 4/2009 | Melville | A61B 1/0008 385/137 |
| 2009/0202201 A1 | * | 8/2009 | Scofet | G02B 6/4206 385/27 |
| 2010/0195957 A1 | * | 8/2010 | Roos | G02B 6/3813 385/29 |
| 2010/0210911 A1 | * | 8/2010 | Shimotsu | A61B 1/00096 600/178 |
| 2011/0044056 A1 | * | 2/2011 | Travis | G02B 6/0053 362/311.02 |
| 2011/0110625 A1 | * | 5/2011 | Chatigny | H01S 3/06704 385/29 |
| 2013/0011102 A1 | * | 1/2013 | Rinzler | G02B 6/3813 385/89 |
| 2014/0073950 A1 | * | 3/2014 | Akui | A61B 1/00172 600/478 |
| 2014/0114131 A1 | * | 4/2014 | Sakai | G02B 21/0028 600/182 |
| 2014/0212091 A1 | | 7/2014 | Hasegawa et al. | |
| 2015/0049983 A1 | * | 2/2015 | Fisher | B32B 37/12 385/29 |
| 2016/0320564 A1 | * | 11/2016 | Murashima | G02B 3/0087 |

FOREIGN PATENT DOCUMENTS

| | | |
|---|---|---|
| JP | 2011-033691 A | 2/2011 |
| JP | 2013-167674 A | 8/2013 |
| JP | 2014-044265 A | 3/2014 |

* cited by examiner

SCANNING ENDOSCOPE HAVING PROPAGATION PORTION WITH LIGHT ABSORBING PORTION OR LIGHT REFLECTING PORTION ON DISTAL END FACE THEREOF

CROSS REFERENCE TO RELATED APPLICATION

This application is a continuation application of PCT/JP2015/073867 filed on Aug. 25, 2015 and claims benefit of Japanese Application No. 2014-239158 filed in Japan on Nov. 26, 2014, the entire contents of which are incorporated herein by this reference.

BACKGROUND OF THE INVENTION

1. Field of the Invention

The present invention relates to a scanning endoscope that detects and images return light of illuminating light irradiating an object while scanning an illumination fiber.

2. Description of the Related Art

An electronic endoscope is known that photoelectrically converts an object image by means of an image pickup apparatus having a solid-state image pickup device such as a CCD or a CMOS, and displays an image of the object on a monitor. Further, an optical scanning endoscope apparatus is known as an apparatus that displays an image of an object without using the technology of a solid-state image pickup device. An optical scanning endoscope picks up an image of an observation target region by continuously receiving reflected light while scanning light that is irradiating a minute point on the observation target region.

In Japanese Patent Application Laid-Open Publication No. 2008-165236, an endoscope and an optical fiber system are described which include a scanning optical fiber having an optical fiber that has a core that transmits an illuminating light and at least one cladding that covers the core and transmits reflected light from an object, and at least one photo sensor that detects reflected light.

SUMMARY OF THE INVENTION

A scanning endoscope according to one aspect of the present invention includes: an optical fiber that propagates an illuminating light radiated from a light source portion and, from a distal end, emits the illuminating light that is propagated; an actuator that causes the distal end of the optical fiber to oscillate in order to scan the illuminating light on an observation target; a fixing portion that fixes the optical fiber to cause the distal end of the optical fiber to be oscillated by the actuator; and a propagation portion that is provided in close contact with an outer circumferential face of a cladding of the optical fiber at a position on a distal end side relative to the fixing portion, and on which, among the illuminating light, light that reaches the outer circumferential face of the cladding is incident and is propagated or absorbed inside the propagation portion.

DETAILED DESCRIPTION OF THE PREFERRED EMBODIMENT

Hereunder, an embodiment of the present invention is described with reference to the attached drawings.

Note that the respective drawings used for the following description are drawings that schematically illustrate the present invention, and with respect to the dimensional relation and contraction scale and the like of the respective members, the contraction scale is varied for each component so as to be shown in a size that is recognizable in the drawings. Further, the present invention is not limited only to the quantity of components, the shapes of components, the ratios between the sizes of components, and the relative positional relationship between the respective components illustrated in the drawings.

Figure 1:
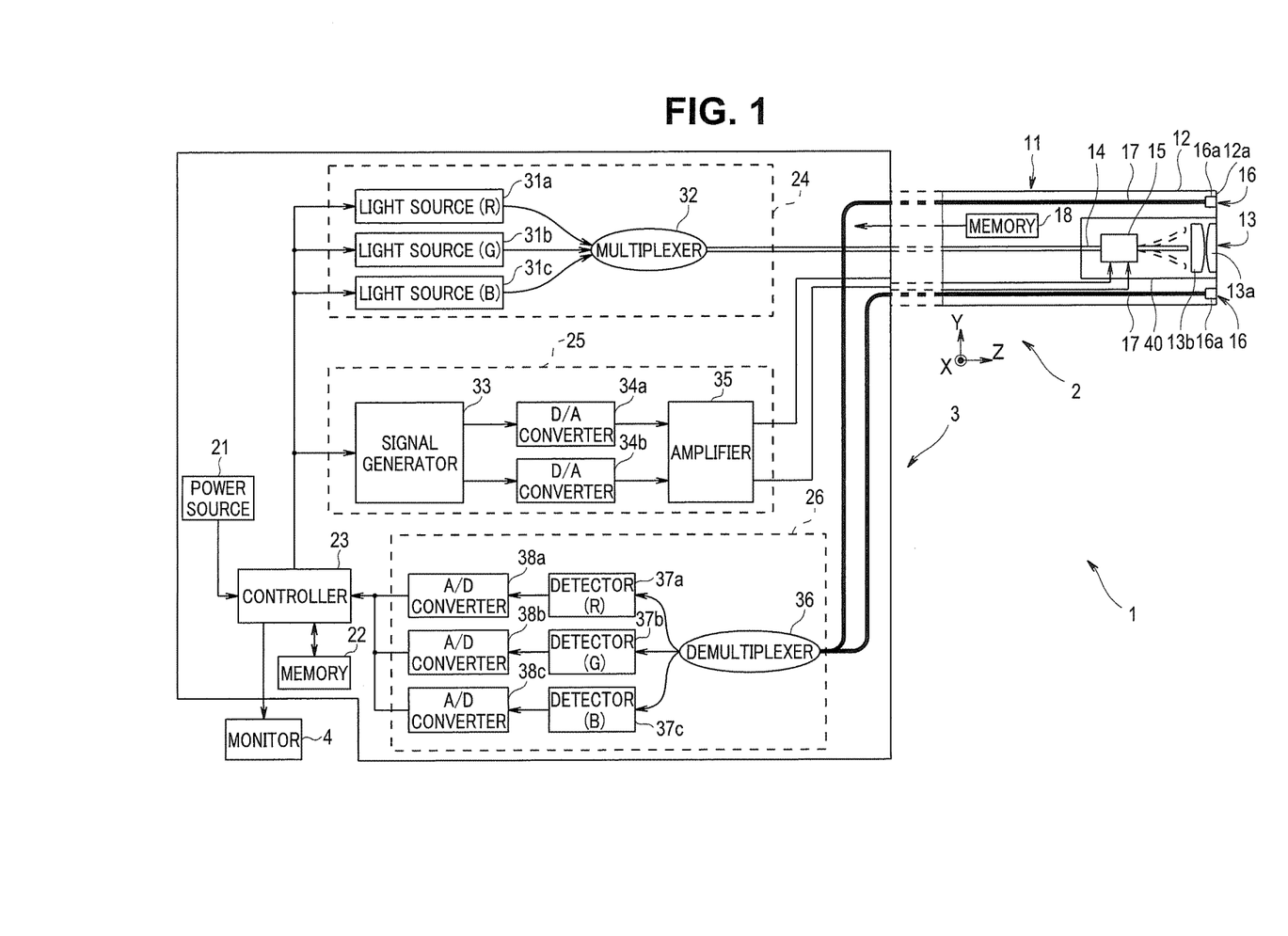
FIG. 1 is a view for describing a scanning endoscope apparatus.

As shown in FIG. 1, a scanning endoscope apparatus 1 includes a scanning endoscope (hereunder, referred to simply as "endoscope") 2, a main body apparatus 3 to which the endoscope 2 is connected, and a monitor 4.

The endoscope 2 radiates an illuminating light at a subject while scanning the illuminating light, and obtains return light from the subject. A subject image that is generated by the main body apparatus 3 is displayed on the monitor 4.

The endoscope 2 has an elongated insertion portion 11 that is inserted through the inside of a living organism. The insertion portion 11 is configured mainly with a tube body having predetermined flexibility. A distal end portion 12 is provided on the distal end side of the insertion portion 11.

A connector and the like which are not shown in the drawing are provided on the proximal end side of the insertion portion 11. The endoscope 2 is configured to be detachably connectable to the main body apparatus 3 via the connector and the like.

A distal end illumination lens 13a that is an optical member which is included in an illuminating optical system 13, and a condenser lens 16a that is an optical member which is included in a detection optical system 16 are provided at a distal end face 12a of the distal end portion 12.

Reference character 13b denotes a second illumination lens that is one of the optical members constituting the illuminating optical system 13. The second illumination lens 13b is constituted by one or a plurality of optical lenses. The detection optical system 16 has the condenser lens 16a and a detection fiber 17.

Inside the insertion portion 11 are provided the illuminating optical system 13, an illumination fiber 14 and an actuator 15 which constitute a light scanning unit 40, the detection fiber 17, an endoscope memory 18 and the like.

Various kinds of information relating to the endoscope 2 are stored in the endoscope memory 18. When the endoscope 2 is connected to the main body apparatus 3, the endoscope memory 18 is connected to a controller 23, described later, via an unshown signal wire.

A configuration is adopted so that, in the connected state described above, the various kinds of information stored in the endoscope memory 18 are read by the controller 23.

The illumination fiber 14 propagates an illuminating light that is emitted from a light source unit 24 serving as a light source portion that is provided in the main body apparatus 3, and emits the propagated illuminating light from a distal end face. The illuminating light emitted from the distal end face of the fiber passes through the illuminating optical system 13 and travels in the direction of an object that is an observation target.

The detection fiber 17 is inserted through the insertion portion 11, along an inner circumference. The detection fiber 17 transmits return light from the observation target which is received by the condenser lens 16a to a detection unit 26 that is described later. That is, the condenser lens 16a is arranged at a distal end of the detection fiber 17.

Note that the detection fiber 17 is a fiber bundle which includes at least two fibers. When the endoscope 2 is connected to the main body apparatus 3, the detection fiber 17 is connected to a demultiplexer 36 that is described later.

Figure 2:
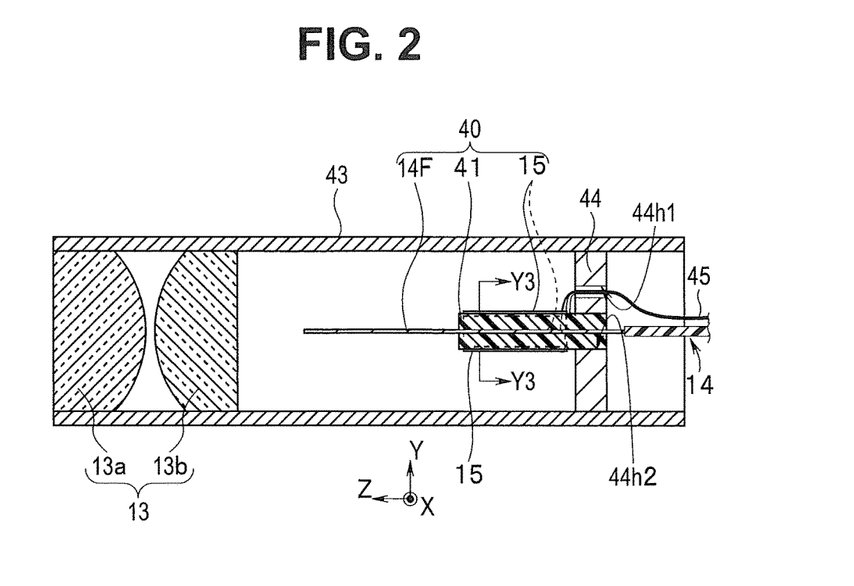
FIG. 2 is a view for describing the configuration of a distal end portion of an insertion portion and a light scanning unit of the scanning endoscope.
Figure 3:
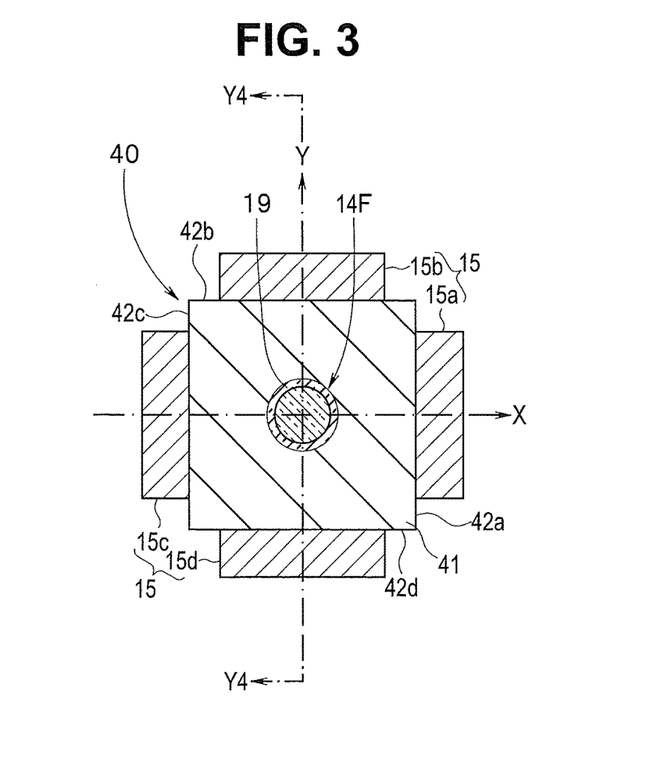
FIG. 3 is a cross-sectional view along a line indicated by arrows Y3-Y3 in FIG. 2.
Figure 4:
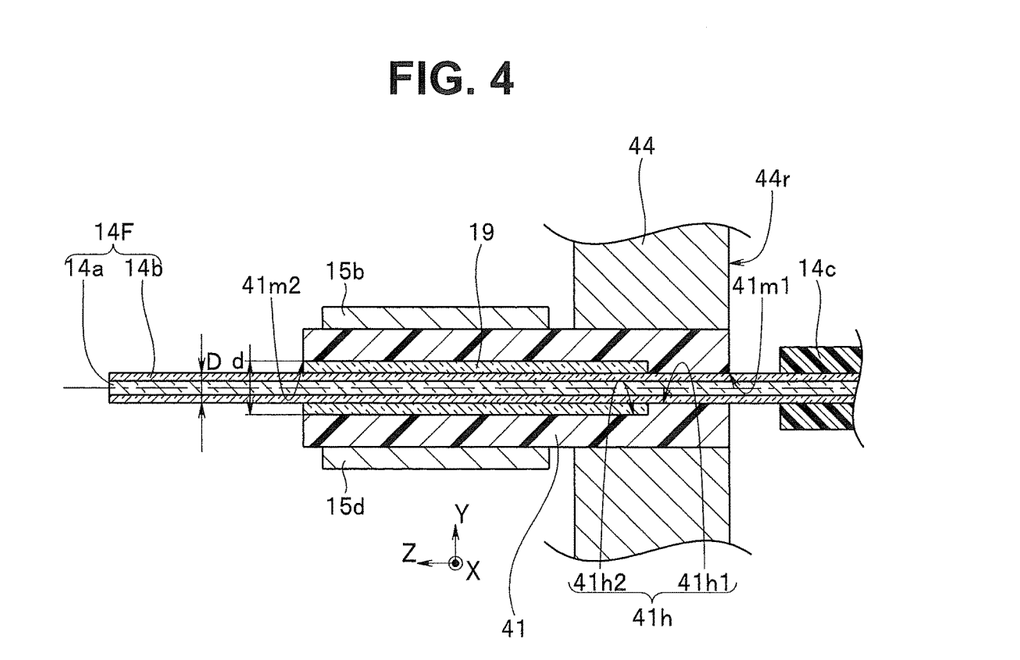
FIG. 4 is a cross-sectional view along a line indicated by arrows Y4-Y4 in FIG. 3.

As shown in FIG. 2 to FIG. 4, a covering 14c is peeled off at the distal end side of the illumination fiber 14 to expose a cladding 14b. Reference character 14a denotes a core. The cladding 14b is provided around the core 14a, along a central axis of the core 14a. As is known, the refractive index of the cladding 14b is set so as to be lower than the refractive index of the core 14a.

Note that a distal end face of the covering 14c is disposed so as to be separated by a predetermined distance from a proximal end side 44a of a fixing block 44. In the following description, the exposed cladding 14b including the core 14a from which the covering 14c of the illumination fiber 14 is peeled off is referred to as "optical fiber 14F."

The optical fiber 14F is inserted and disposed inside a ferrule 41 as a fiber holding portion, and is held by the ferrule 41.

Note that the ferrule 41 is formed of a material such as zirconia or nickel on which hole machining that corresponds to an external diameter (for example, 125 μm) of the illumination fiber 14 can be performed easily and with high accuracy (for example, ±1 μm).

In the present embodiment, the ferrule 41 is a non-conductive material such as zirconia, and for example is a quadrangular prism. The ferrule 41 has side faces 42a and 42c that are perpendicular to an X-axis direction, and side faces 42b and 42d that are perpendicular to a Y-axis direction.

Note that, a longitudinal axis direction of the insertion portion 11 is defined as a Z-axis direction, and the two directions which are orthogonal to the Z-axis direction and are orthogonal to each other are defined as the X-axis direction and the Y-axis direction.

A stepped through-hole 41h is formed along the central axis in the ferrule 41. A hole for a fiber 41h1 as a first hole, and a hole for a medium 41h2 as a second hole are provided in the stepped through-hole 41h. The hole for a medium 41h2 is located on a distal end side of the ferrule 41, and has a larger diameter than the first hole.

The inner diameter of the hole for a fiber 41h1 is formed to be slightly larger than the external diameter of the optical fiber 14F. A predetermined clearance is set between the hole for a fiber 41h1 and the optical fiber 14F.

After being inserted through the inside of the hole for a fiber 41h1 from a proximal end opening 41m1 of the stepped through-hole 41h, the optical fiber 14F passes through the hole for a fiber 41h1 and the hole for a medium 41h2 and is extended by a predetermined distance from a distal end opening 41m2 of the through-hole 41h.

An inner diameter d of the hole for a medium 41h2 is formed to be larger by a predetermined dimension than an external diameter D of the cladding 14b constituting the optical fiber 14F. An adhesive 19 having a low conductivity of a level such that light that leaks from the fiber does not specularly reflect and which can serve as a high refractive index medium having a refractive index that is greater than the refractive index of the cladding 14b is filled in a gap between the hole for a medium 41h2 and the optical fiber 14F.

As a result of the adhesive 19 setting, a distal end side portion of the optical fiber 14F that is extended from the distal end opening 41m2 is fixedly supported in a cantilevered state by the ferrule 41.

The adhesive 19 is a propagation member and is a transparent adhesive such as a heat setting adhesive or ultraviolet setting adhesive, and is filled into the gap between the hole for a medium 41h2 and the optical fiber 14F in the state of a liquid having a predetermined viscosity and then sets to function as a propagation portion. The set adhesive 19 closely contacts the outer circumferential face of the optical fiber 14F and the inner circumferential face of the hole for a medium 41h2 and enters a fixed state. Further, the refractive index of the set adhesive 19 is greater than the refractive index of the cladding 14b.

The fixing block 44 is a fixing portion at which the proximal end side of the ferrule 41 is fixedly installed. The fixing block 44 is a circular disc shape that has a predetermined thickness. A lead wire insertion hole 44h1 and a ferrule mounting hole 44h2 are formed in the fixing block 44.

A plurality of lead wires 45 are inserted through and disposed in the lead wire insertion hole 44h1. The proximal end portion of the ferrule 41 is fitted into and disposed in the ferrule mounting hole 44h2, and is integrally fixed to the ferrule mounting hole 44h2 by, for example, adhesion.

In this fixed state, a boundary between the hole for a fiber 41h1 and the hole for a medium 41h2 is configured so as to be positioned further on the distal end side than a proximal end side 44r of the fixing block 44.

The fixing block 44 to which the ferrule 41 is fixed is integrally fixed by adhesion or the like at a predetermined position on a proximal end side of a frame body 43. In the integrally fixed state, a central axis of the fixing block 44 and a central axis of the frame body 43 coincide.

Note that, in the present embodiment, a configuration is adopted so that, by placing the proximal end side of the ferrule 41 and the proximal end side 44r of the fixing block 44 in a flush state, the distal end face of the optical fiber 14F in the cantilevered state is disposed at a predetermined position in the longitudinal direction of the frame body 43.

The actuator 15 is, for example, a piezoelectric element. In the present embodiment, the actuator 15 is constituted by four actuators 15a, 15b, 15c and 15d. The respective actuators 15a, 15b, 15c and 15d are provided at predetermined positions on the distal end side of the illumination fiber 14. The respective actuators 15a, 15b, 15c and 15d are provided at positions that are adjacent to the respective side faces 42a, 42b, 42c and 42d of the ferrule 41, and are respectively point symmetrical at 90°.

That is, the ferrule 41 is arranged between the actuator 15 and the illumination fiber 14.

The actuators 15a, 15b, 15c and 15d have a configuration in which electrodes are provided on two separated surfaces of a piezoelectric element (a piezo element), and expand and contract in response to a drive signal from a driver unit 25 that is described later.

The respective actuators 15a, 15b, 15c and 15d apply a vibration to the ferrule 41 to cause the distal end of the illumination fiber 14 to oscillate and scan the distal end of the illumination fiber 14 in an elliptic spiral shape.

The illumination fiber 14, the ferrule 41 and the actuator 15 constitute the light scanning unit 40 that is a scanning portion.

Note that, a resonance frequency that causes the illumination fiber 14 to oscillate significantly is determined by the diameter of the illumination fiber 14 and a length of the free end that is a protruding length from the distal end face of the ferrule 41.

The respective actuators 15a, 15b, 15c and 15d are not limited to piezoelectric transducers that are each constituted by a piezoelectric element having a pair of electrodes, and may be, for example, coil-type transducers that are electromagnetically driven.

As a GND electrode for the respective actuators 15a, 15b, 15c and 15d, when the ferrule 41 is a nonconductive material, the surface of the ferrule 41 is subjected to conductive film formation and is used as the GND electrode. In contrast, when a conductive material such as nickel is used for the ferrule 41, the ferrule 41 itself is used as the GND electrode.

Further, in the above description the ferrule 41 is described as a quadrangular prism. However, the shape of the ferrule 41 is not limited to a quadrangular prism, and for example the ferrule may be a cylindrical shape or may have a prismatic shape of any kind.

As shown in FIG. 1, a power source 21, a main body memory 22, the controller 23, the light source unit 24, the driver unit 25, the detection unit 26 and the like are provided in the main body apparatus 3.

The light source unit 24 includes three light sources 31a, 31b and 31c, and a multiplexer 32.

The driver unit 25 includes a signal generator 33, digital/analog (hereunder, referred to as "D/A") converters 34a and 34b, and an amplifier 35.

The detection unit 26 includes the demultiplexer 36, detectors 37a, 37b and 37c, and analog/digital (hereunder, referred to as "A/D") converters 38a, 38b and 38c.

The power source 21 supplies power to the controller 23 in accordance with operation of an unshown power source switch or the like.

The main body memory 22 stores a control program and the like for performing overall control of the main body apparatus 3.

When the supply of power from the power source 21 is started, the controller 23 reads the control program from the main body memory 22 and performs control of the light source unit 24, the driver unit 25 and the detection unit 27.

Based on control of the controller 23, the light sources 31a, 31b and 31c of the light source unit 24 emit light of respectively different wavelength bands, for example, light of the wavelength bands of R (red), G (green) and B (blue) to the multiplexer 32. The multiplexer 32 multiplexes the lights of the wavelength bands of R, G and B that are emitted from the light sources 31a, 31b and 31c, and emits the resultant light towards the illumination fiber 14.

The signal generator 33 of the driver unit 25 outputs a drive signal for causing the distal end of the illumination fiber 14 to scan in a desired direction, for example, in an elliptic spiral shape, based on the control of the controller 23.

The signal generator 33 outputs a drive signal for driving the distal end of the illumination fiber 14 in a lateral direction (X-axis direction) with respect to the longitudinal axis of the insertion portion 11 to the first D/A converter 34a, and outputs a drive signal for driving the distal end of the illumination fiber 14 in a vertical direction (Y-axis direction) with respect to the insertion axis of the insertion portion 11 to the second D/A converter 34b.

The D/A converters 34a and 34b convert the respectively inputted drive signals from digital signals to analog signals, and output the analog signals to the amplifier 35. The amplifier 35 amplifies the inputted drive signals and outputs the amplified drive signals to the actuator 15.

In the present embodiment, the two actuators 15a and 15c as a first driving portion drive in accordance with a drive signal from the D/A converter 34a, and the other two actuators 15b and 15d as a second driving portion drive in accordance with a drive signal from the D/A converter 34b to cause the distal end that is the free end of the illumination fiber 14 to oscillate and scan in an elliptic spiral shape.

Thus, the light emitted from the light source unit 24 to the illumination fiber 14 is sequentially emitted in an elliptic spiral shape to the subject that is the observation target.

After the light is emitted to the subject, a return light that is reflected on a surface region of the subject is guided to the demultiplexer 36 of the detection unit 26 by the detection fiber 17. The demultiplexer 36 is, for example, a dichroic mirror, and demultiplexes the return light in predetermined wavelength bands.

The demultiplexer 36 demultiplexes the return light that is guided by the detection fiber 17 into return lights of the wavelength bands of R, G and B, and outputs the return lights to the detectors 37a, 37b and 37c, respectively.

The detectors 37a, 37b and 37c detect the light intensities of the return lights of the R, G and B wavelength bands, respectively. Signals of the light intensities detected by the detectors 37a, 37b and 37c are outputted to the A/D converters 38a, 38b and 38c, respectively. The A/D converters 38a, 38b and 38c convert the signals of the light intensities respectively outputted from the detectors 37a, 37b and 37c from analog signals to digital signals, and output the digital signals to the controller 23.

The controller 23 performs predetermined image processing on the digital signals from the A/D converters 38a, 38b and 38c to generate an object image, and displays the object image on the monitor 4.

The operation of the light scanning unit 40 provided inside the distal end portion 12 of the insertion portion 11 will now be described.

By the optical fiber 14F being inserted and disposed in the hole for a fiber 41h1 formed in the ferrule 41, stress is liable to be applied to the optical fiber 14F disposed in the vicinity of the proximal end side 44r of the fixing block 44. In a case where stress is applied to the optical fiber 14F and the optical fiber 14F is deformed, unnecessary mode light is generated, and the base mode light is propagated through the inside of the core 14a, and the unnecessary mode light is propagated through the inside of the cladding 14b and travels towards the distal end face of the optical fiber 14F.

In the present embodiment, the adhesive 19 that is set and whose refractive index is greater than the refractive index of the cladding 14b is provided in a closely contacting state on the outer circumferential face of the optical fiber 14F that is inserted through the hole for a medium 41*h*2 of the ferrule 41.

Accordingly, the unnecessary mode light that is propagated through the inside of the cladding 14*b* enters the adhesive 19 from the interface between the cladding 14*b* and the adhesive 19 and is thus removed from inside the cladding 14*b*. As a result, the base mode light that propagates through inside the core 14*a* can be mainly emitted from the distal end face of the optical fiber 14F.

Therefore, in a scanning state in which the optical fiber 14F that is supported in a cantilevered state is caused to oscillate, illuminating light having a small spot size and a light intensity distribution that is a Gaussian distribution is sequentially emitted in an elliptic spiral shape to the subject that is the observation target from the distal end face of the optical fiber 14F, and a favorable observed image of the observation target that has a high resolution can be obtained.

Note that, in the above described embodiment, a configuration is adopted in which the adhesive 19 having a low conductivity of a level such that light that leaks from the fiber does not specularly reflect and which has a refractive index that is greater than the refractive index of the cladding 14*b* is filled in a gap between the hole for a medium 41*h*2 and the optical fiber 14F. However, the following configurations may also be adopted.

A filler that absorbs unnecessary mode light is mixed into the adhesive 19. As a result, unnecessary mode light that entered the adhesive 19 from the cladding 14*b* is absorbed by the filler, and thus the unnecessary mode light propagating through the inside of the adhesive 19 decreases. Note that, instead of mixing filler that absorbs unnecessary mode light into the adhesive 19, a configuration may be adopted so as to obtain a similar action and effect by blackening the inner face of the hole for a medium 41*h*2 so as to absorb unnecessary mode light.

Figure 5:
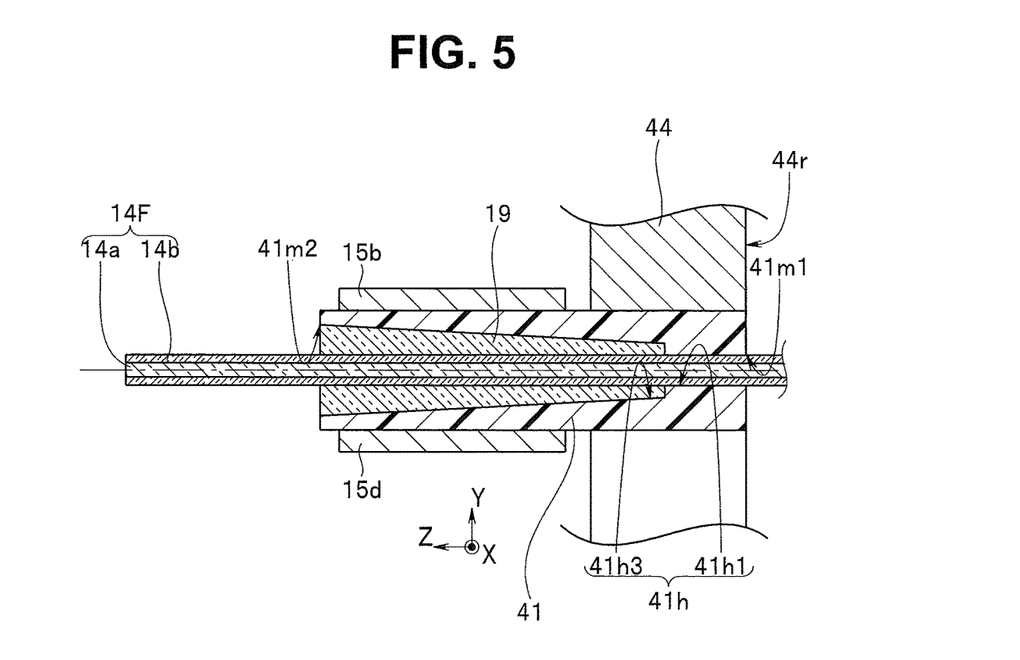
FIG. 5 is a view for describing a configuration example in which a hole for a medium is provided which has a tapered face whose inner diameter continuously changes to a smaller diameter in a proximal end direction from a distal end opening side.

Further, as shown in FIG. 5, the inner face of a hole for a medium 41*h*3 is configured as a tapered face having an inner diameter that continuously changes to a smaller diameter from the distal end opening 41*m*2 side in a proximal end direction of the central axis. The adhesive 19 is provided by being filled in a gap between the hole for a medium 41*h*3 and the optical fiber 14F, and the adhesive 19 sets.

According to this configuration, unnecessary mode light that enters from the interface between the cladding 14*b* and the adhesive 19 is reflected at the inclined interface between the adhesive 19 and the inner face of the hole for a medium 41*h*3, and the angle of reflection is changed each time as the unnecessary mode light is repeatedly reflected. As a result, re-entry of the unnecessary mode light into the cladding 14*b* can be prevented.

Further, a configuration may also be adopted so as to absorb unnecessary mode light by mixing the above described filler into the adhesive 19 or blackening the inner face of the hole for a medium 41*h*3.

Figure 6A:
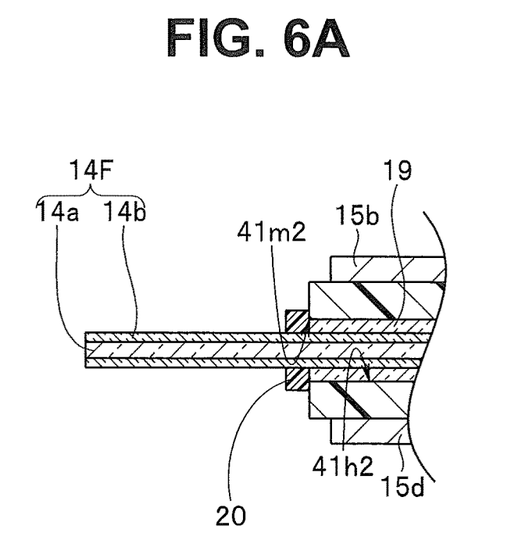
FIG. 6A is a view for describing a light scanning unit in which an annular member that blocks a distal end opening of a hole for a medium is provided.
Figure 6B:
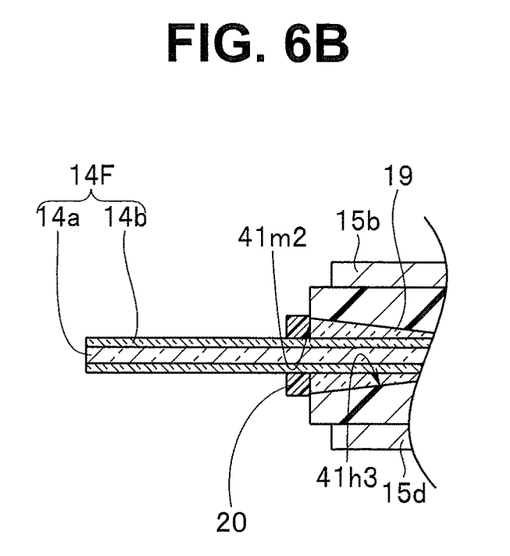
FIG. 6B is a view for describing a light scanning unit in which an annular member that blocks a distal end opening of a hole for a medium is provided.

Furthermore, as shown in FIG. 6A and FIG. 6B, an annular member 20 is provided that blocks the distal end opening 41*m*2 of the hole for a medium 41*h*2 or 41*h*3 formed in ferrule 41, to prevent the leakage of light. The annular member 20 is a light absorbing portion that absorbs unnecessary mode light or is a light reflecting portion that reflects unnecessary mode light, and is integrally bonded and fixed to the adhesive 19.

According to this configuration, unnecessary mode light that enters the adhesive 19 and is propagated through the inside of the adhesive 19 can be prevented from being emitted to outside from the distal end face of the adhesive.

Note that, in FIG. 6A and FIG. 6B, a predetermined gap is provided between the inner circumferential face of the annular member 20 and the outer circumferential face of the optical fiber 14F to prevent interference with respect to oscillation of the optical fiber 14F.

Note that, a configuration may also be adopted in which the adhesive 19 is applied onto the outer circumferential face of the optical fiber 14F that is extended from the ferrule 41 and set, so that unnecessary mode light that is propagated through inside the cladding 14*b* is caused to enter the adhesive 19 from the interface between the cladding 14*b* and the adhesive 19 and to be removed from the cladding 14*b*.

According to the present invention, a scanning endoscope can be realized that, while removing unnecessary mode light, emits base mode light from a distal end face of an optical fiber for illuminating light that has a configuration that is supported in a cantilevered state by a fiber holding portion, and obtains an observation target image that has a favorable resolution.

The invention described in the foregoing embodiment is not limited to the embodiment and modifications described above, and various modifications can be implemented within a range that does not depart from the spirit and scope of the present invention in the implementing stage.

What is claimed is:

1. A scanning endoscope, comprising:
   an optical fiber that propagates an illuminating light radiated from a light source portion and, from a distal end, emits the illuminating light that is propagated;
   an actuator that causes the distal end of the optical fiber to oscillate in order to scan the illuminating light on an observation target;
   a fixing portion that fixes the optical fiber to cause the distal end of the optical fiber to be oscillated by the actuator;
   a propagation portion that is provided in close contact with an outer circumferential face of a cladding of the optical fiber at a position on a distal end side relative to the fixing portion, and on which, among the illuminating light, light that reaches the outer circumferential face of the cladding is incident and is propagated or absorbed inside the propagation portion; and
   one of a light absorbing portion that absorbs light or a light reflecting portion that reflects light is provided on a distal end face of the propagation portion.

2. The scanning endoscope according to claim 1, wherein the propagation portion is a high refractive index medium which has conductivity of a level that does not specularly reflect light that is incident, and has a refractive index that is greater than a refractive index of the cladding.

3. The scanning endoscope according to claim 1, further comprising a fiber holding portion that is provided between the actuator and the optical fiber and is fixed by the fixing portion.

4. The scanning endoscope according to claim 3, wherein the propagation portion is provided in close contact with the outer circumferential face of the cladding inside the fiber holding portion.

5. The scanning endoscope according to claim 4, wherein the fiber holding portion has an opening on a distal end side, and has a hole for a medium having an inner diameter which is larger by a predetermined dimension than an external diameter of the cladding of the optical fiber.

6. The scanning endoscope according to claim 5, wherein the inner diameter of the hole for a medium of the fiber holding portion progressively changes to a smaller diameter in a proximal end direction along a central axis from a distal end opening side.

7. The scanning endoscope according to claim 3, wherein the propagation portion sets from a liquid state that has a predetermined viscosity and is tightly fixed to the outer circumferential face of the cladding and an inner circumferential face of a through-hole of the fiber holding portion.

8. The scanning endoscope according to claim 1, wherein the propagation portion has a light absorption characteristic.

9. The scanning endoscope according to claim 1, further comprising an optical system that condenses a return light from the observation target.

* * * * *